(12) United States Patent
Harmon

(10) Patent No.: US 6,821,738 B2
(45) Date of Patent: Nov. 23, 2004

(54) BROAD SPECTRUM BIO-DETECTION OF NERVE AGENTS, ORGANOPHOSPHATES, AND OTHER CHEMICAL WARFARE AGENTS

(75) Inventor: H. James Harmon, Edmond, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 386 days.

(21) Appl. No.: 09/910,226

(22) Filed: Jul. 20, 2001

(65) Prior Publication Data

US 2002/0031843 A1 Mar. 14, 2002

Related U.S. Application Data

(63) Continuation-in-part of application No. 09/487,559, filed on Jan. 19, 2000, now abandoned.
(60) Provisional application No. 60/116,504, filed on Jan. 20, 1999.

(51) Int. Cl.[7] ............................................. G01N 33/53
(52) U.S. Cl. ............................ 435/7.1; 435/5; 435/7.9; 436/518; 436/172
(58) Field of Search ........................... 436/172, 518, 436/519, 523–535, 512, 514–516, 543–548; 435/4, 5, 7.7, 7.71, 7.72, 7.9, 7.91, 7.92–7.95, 7.1, 7.2; 422/50, 82.05–82.11

(56) References Cited

U.S. PATENT DOCUMENTS

| | | | |
|---|---|---|---|
| 3,659,100 A | | 4/1972 | Anderson et al. |
| 4,360,776 A | * | 11/1982 | Bauman ................... 324/316 |
| 4,361,648 A | | 11/1982 | Shuenn-tzong ............. 435/10 |
| 4,366,866 A | * | 1/1983 | Sweeney ................... 169/37 |
| 4,517,290 A | * | 5/1985 | Iwasa et al. ................ 435/7 |
| 4,650,329 A | | 3/1987 | Barrett et al. |
| 4,675,300 A | * | 6/1987 | Zare et al. ................. 204/452 |
| 4,895,809 A | * | 1/1990 | Schlabach et al. ......... 436/518 |
| 5,063,164 A | | 11/1991 | Goldstein |
| 5,071,770 A | | 12/1991 | Kolesar, Jr. |
| 5,087,556 A | | 2/1992 | Ertinghausen |
| 5,096,671 A | | 3/1992 | Kane et al. |
| 5,156,972 A | | 10/1992 | Issachar |
| 5,165,005 A | | 11/1992 | Klainer et al. |
| 5,230,998 A | * | 7/1993 | Neurath et al. ............. 435/7.1 |
| 5,279,954 A | | 1/1994 | Wagner et al. ............. 435/176 |
| 5,315,673 A | | 5/1994 | Stetter et al. |
| 5,364,797 A | | 11/1994 | Olson et al. |
| 5,368,028 A | | 11/1994 | Palti |
| 5,417,835 A | | 5/1995 | Brown et al. |
| 5,457,313 A | * | 10/1995 | Baylor et al. ............. 250/227.21 |
| 5,501,988 A | * | 3/1996 | Kobayashi et al. ......... 436/548 |

(List continued on next page.)

FOREIGN PATENT DOCUMENTS

| | | | |
|---|---|---|---|
| WO | WO 89/01794 | 3/1989 | ............ A61M/5/00 |
| WO | WO 93/15218 | 8/1993 | ............ C12Q/1/26 |
| WO | WO 95/15760 | 6/1995 | ......... A61K/31/695 |
| WO | WO 96/05847 | 2/1996 | .......... A61K/35/16 |
| WO | WO 98/41872 | 9/1998 | ......... G01N/33/566 |
| WO | WO 00/45149 | 8/2000 | .......... G01N/21/00 |
| WO | WO 01/36665 | 5/2001 | ............ C12Q/1/34 |

Primary Examiner—Christopher L. Chin
Assistant Examiner—Ann Y Lam
(74) Attorney, Agent, or Firm—Fellers, Snider, Blankenship, Bailey & Tippens, P.C.

(57) ABSTRACT

The instant invention pertains generally to a method and apparatus for rapidly detecting nerve agents, organophosphates, and other chemical warfare agents. A sensor has been developed that can be used to rapidly detect multiple analytes such as organic compounds. Analytes can be detected by monitoring changes in the optical properties of the absorbance and/or fluorescence spectra of highly colored heterocyclic compounds such as porphyrins or related compounds such as phthalocyanines. The result is a real-time monitor that is suitable for use in situations where encounter with chemical warfare agents is possible.

14 Claims, 7 Drawing Sheets

U.S. PATENT DOCUMENTS

| | | |
|---|---|---|
| 5,567,624 A | 10/1996 | Smith |
| 5,599,923 A * | 2/1997 | Sessler et al. ............... 540/145 |
| 5,686,237 A * | 11/1997 | Al-Bayati ....................... 435/4 |
| 5,741,686 A * | 4/1998 | Wagner et al. ............... 435/188 |
| 5,891,641 A | 4/1999 | Prusiner et al. ............... 435/7.1 |
| 6,033,913 A * | 3/2000 | Morozov et al. ............. 436/86 |
| 6,203,994 B1 | 3/2001 | Epps et al. .................... 435/7.1 |
| 6,451,311 B2 * | 9/2002 | Althaus et al. .......... 424/158.1 |

* cited by examiner

| TPPS | TPPS |
| --- | --- |
| ABSORBS 413nm | ABSORBS 424nm |

Shape 1 → Shape 2

*Fig. 8*

BROAD SPECTRUM BIO-DETECTION OF NERVE AGENTS, ORGANOPHOSPHATES, AND OTHER CHEMICAL WARFARE AGENTS

RELATED APPLICATIONS

This application is a continuation-in-part of pending U.S. application Ser. No. 09/487,559 filed Jan. 19, 2000 now abandoned, which application claims the benefit of U.S. Provisional Application Ser. No. 60/116,504, filed on Jan. 20, 1999, the disclosures of which are incorporated herein by reference.

STATEMENT REGARDING FEDERALLY SPONSORED RESEARCH

The instant invention was partially supported through grants from the U.S. Navy (N00014-92-J-1096) and the U.S. Army (DAAD 05-98-P-1946). The U.S. government may have rights in this invention.

TECHNICAL FIELD

The present invention relates to real-time or near real-time detection in gases or fluids of nerve agents of the sort commonly encountered in chemical warfare agents.

BACKGROUND

Often referred to as the "poor man's nuclear weapon", chemical and biological weapons of war are so named because they cost much less than real nuclear weapons to develop, do not require a high level of technology to produce, and can potentially kill enormous numbers of people. Indeed, unlike nuclear weapons, which require a large, specialized, and costly scientific-industrial base, chemical and biological agents can be made with commercial equipment generally available to any country. Weapons of this sort are especially attractive for use by developing countries against super powers, as they tend to level the playing field in struggles against these better armed and trained opponents. The use of biological and chemical weapons of mass destruction is banned by international treaty, but reports of suspected and confirmed use continue.

Biological weapons can be produced from widely available pathogens which may be procured for legitimate biomedical research or obtained from soil or infected animals and humans. Moreover, many of the infectious diseases associated with biological warfare are endemic to most of the states suspected of developing a biological weapon capability. Biological agents are thus both cheap and easy to obtain: in effect, any nation with a basic pharmaceutical industry—or even a facility such as a brewery—has the capability of producing biological weapons.

Biological agents contain either living organisms or their derivatives, such as toxins, which cause disease or death in humans, animals, or food crops. Living organisms multiply within the living targets to produce their effects, whereas toxins cannot reproduce themselves. Toxins are generally more lethal, and act relatively quickly causing incapacitation or death within minutes or hours. Living organisms (microbial pathogens), require incubation periods of from 24 hours to 6 weeks between infection and appearance of symptoms. This incubation period places limits on their battlefield utility, but it also means that biological weapons can continue to have a significant impact many weeks after the initial attack (e.g., by causing a long-term pandemic). Likewise, this delayed incubation period may mean that a biological attack can be completed before those on the ground have realized that it has occurred, or even take place entirely covertly, the effects being confused with a natural outbreak of disease.

Biological agents are odorless, tasteless, and when dispersed in an aerosol cloud, are invisible to the human eye because the particle size of the aerosol is extremely small— as small as 1 to 5 micrometers or microns. Weight-for-weight, biological weapons are hundreds to thousands of times more potent than the most lethal chemical weapon, meaning that even small amounts (e.g., a few kilograms) could be used with devastating effect, whereas hundreds or thousands of tons of chemical agents could be required for militarily significant operations.

Among lethal chemical warfare agents, nerve agents have played a dominant role since the Second World War. Nerve agents are so-called because they affect the transmission of nerve impulses within the nervous system. Nerve agents belong chemically to the group of organo-phosphorus ("OP", hereinafter) compounds. OP compounds are stable, easily dispersed, highly toxic, and take effect rapidly both when absorbed through the skin and via respiration. They can be manufactured by means of fairly simple chemical techniques and the raw materials to manufacture them are inexpensive and generally readily available. Sarin, one of the more familiar nerve agents, dates from the Second World War and is considered a "classic" substance. In the mid-1950's, however, a group of more stable nerve agents known was the V-agents were developed, with VX being one of the more successful variants. These later-day chemical weapons are approximately ten-fold more poisonous than sarin and are thus among the most toxic substances ever synthesized.

Nerve agents in pure state are colorless liquids with volatiles that vary depending on the particular compound. The consistency of VX may be likened to a non-volatile oil and is therefore classified as belonging to the group of persistent chemical warfare agents. It enters the body mainly through direct contact with the skin. Sarin is at the opposite extreme, being a relatively volatile liquid (comparable with, e.g., water), and is mainly taken up through the respiratory organs.

The nerve agent, either as a gas, aerosol or liquid, enters the body through inhalation or through the skin. Poisoning may also occur through consumption of liquids or foods contaminated with nerve agents. The route through which the poison enters the body largely determines the time required for the nerve agent to begin having an effect. It also influences the symptoms developed and, to some extent, the sequence of the different symptoms. Generally, poisoning takes place more rapidly when the agent is absorbed through the respiratory system than when it enters via other routes such as the skin. This is because the lungs contain numerous blood vessels which provide for rapid assimilation and transmission to the target organs. Nerve agents are more or less fat-soluble and can penetrate the outer layers of the skin. However, it takes some time before the poison reaches the deeper blood vessels. Consequently, the first symptoms may not appear until 20–30 minutes after the initial exposure. Chemically, nerve agents act by binding to an enzyme in the body of the victim, acetylcholinesterase, which inhibits this vital enzyme's normal biological activity in the cholinergic nervous system. Acetylcholinesterase ("AChE") terminates nerve impulse transmission at cholinergic synapses by hydrolyzing the neurotransmitter acetylcholine to acetate and choline. Organophosphate compounds such as insecticides and nerve agents inhibit AChE, which inhibition results in a build up of acetylcholine, thereby causing constant transmission of nerve signals.

Most recent research in the area of chemical and biological weapons has been focused on the detection and treatment of exposed individuals rather than the creation of new agents. Because the length of time that an individual is exposed to the agent can be determinative of the likelihood of successful treatment, rapid recognition that an exposure has occurred may mean the difference between life and death. Of course, this recognition/identification time includes not only the time required to perform the necessary diagnostic or chemical tests, but also the time required to move the victim or exposed item to a testing station or facility (or to move the testing unit to the victim, in some cases).

Certainly, there are any number of methods for detecting specific oganophosphate compounds in water or air. However, the methods suggested heretofore for are either too slow to make them useful for real time detection, or too bulky to be easily transported to a location near the front lines, where an attack would normally first be registered. For example, one common method of determining the presence of an OP compound is to measure the biochemical activity of acetylcholinesterase; if OP is present, the activity per enzyme molecule present decreases. However, this method is very slow and it might require days to get the sample to the lab and complete the tests. Additionally, even if conventional transportable units were fast enough to make them useful in real-time, they are too bulky to be distributed to and carried by every soldier which would be, of course, the best method of distribution. Further, most traditional methods of detecting nerve-type agents are designed to respond to one (or a few) specific compounds, which creates certain risks for in-field use, where the particular nerve gas variant might be different than expected Heretofore, as is well known in the chemical and biological warfare arts, there has been a need for a method and apparatus that provides for rapid detection of nerve agents such as organophosphate compounds ("OP" compounds, hereinafter). This method should operate quickly and reliably to provide identification at the earliest possible moment, preferably in real-time or nearly so. It should work to detect these compounds in air or water and be portable and inexpensive enough to be issued to each individual who is at risk of exposure. Finally, it should a broad band detector which is responsive to a wide variety of OP compounds. Accordingly, it should now be recognized, as was recognized by the present inventor, that there exists, and has existed for some time, a very real need for an invention that would address and solve the above-described problems.

Before proceeding to a description of the present invention, however, it should be noted and remembered that the description of the invention which follows, together with the accompanying drawings, should not be construed as limiting the invention to the examples (or preferred embodiments) shown and described. This is so because those skilled in the art to which the invention pertains will be able to devise other forms of this invention within the ambit of the appended claims.

SUMMARY OF THE INVENTION

According to a first preferred aspect of the instant invention, there is provided a method for detecting the presence of nerve agents, OP compounds, and other molecules, including pesticides by detecting an alteration of the electron configuration and spectral properties of porphyrins and porphyrin surfaces and, recognizing the changes in protein conformation which are evidenced by alteration of porphyrins or other colorimetric indicators complexed with the protein. In brief, this embodiment of the instant invention detects an analyte by measuring the conformational change of its specific binding protein.

The instant invention is founded on the observation that complexes of protein with colorimetric compounds can be used to detect the presence of very low concentrations of hazardous or chemical warfare agents. Changes in the spectrum of a properly chosen colorimetric compound can be used as a "real-time" indicator to detect the presence of a broad range of dangerous substances such as nerve agents, organophosphates, and other chemical warfare agents. By way of general explanation and according to a first preferred embodiment, it is well known, and will be further discussed in the following narrative, that the electron distribution in a colorimetric compound is altered by its immediate environment. Changes in electron distribution result in corresponding changes in the spectrum of the colorimetric indicator. Thus, an indicator for use in detecting hazardous compounds may be created by monitoring specific lights wavelengths in the spectrum of a colorimetric compound of choice. Further, because of the multiplicity of absorbance bands in various of these indicators, unique spectral "signatures" may be developed for use in subsequent detection.

Measurements of the optical changes in the colorimetric indicator are preferably made using both absorbance and fluorescence spectroscopy in the visible (400–800 nm) region. However, rather than attempt to directly sense changes in the spectrum of the indicator, difference spectra are preferably used instead, a difference spectrum being defined to be the spectrum of the indicator following exposure to an analyte minus the spectrum of the indicator prior to exposure. Wavelength shifts as small as 1–2 nm and absorbance changes down to or below 0.005A can be identified using the difference spectrum, thereby making it possible to identify over 7700 different analytes and quantify their concentration levels down to the $10^{-9}$ M range.

Binding of substrate as well as inhibitors of enzymes may induce conformational changes in the enzyme. As is described hereinafter, changes in protein conformation induced by a substrate/inhibitor can be detected by porphyrins. More particularly, the change in conformation of acetylcholine esterase (the principal target for nerve agents and pesticides) upon binding of inhibitors is detected by colorimetric indicators such as porphyrins. Enzymes can be immobilized and complexed with porphyrins to make a solid-state monolayer reactive thin film sensor surface whose optical properties can readily be detected.

Additionally, and according to another preferred embodiment, there is provided a method and apparatus for the detection of nerve agents, OP compounds, and other molecules, including pesticides, which utilizes a reversible competitive inhibitor in combination with changes in the spectrum of the detecting materials to create a real-time sensor. More specifically, according to a preferred embodiment, an AChE-based biosensor is created by binding to the AChE molecule a porphyrin which inhibits it and which reversibly binds at the active site where substrate and/or nerve gasses and other inhibitors will bind. One such preferred porphyrin is $TPPS_1$ (i.e., monosulfonate tetraphenyl porphyrin). When such a biosensor is exposed to nerve agents, etc., the OP compound will displace the selected porphyrin, thereby resulting in a change in the spectral properties of the biosensor.

According another aspect of the instant invention, there is provided an apparatus for detecting materials such as nerve agents, pesticides, and OP compounds, which uses real-time measurement of the changing spectral characteristics of a substrate as an indication of the presence of these materials. More particularly, the instant apparatus monitors the changing optical spectrum of a specially prepared colorimetrically responsive surface which indicates the presence of materials such as organophosphates through changes in its spectrum. Broadly speaking, the instant apparatus consists of a light source (preferably emitting light in the 400 nm to 800 nm range); a colorimetrically responsive surface which is illuminated by the irradiating light source; and, an optically sensitive detector which is directed toward the illuminated surface. In the preferred embodiment, the light source/detector combination operates continuously so that changes in the absorptive properties of the detection surface are immediately identified. It should be noted that the instant invention can be made small enough to take the form of a badge or similar device that might be worn continuously by at-risk personnel, and this device might also incorporate some sort of warning mechanism to notify the wearer the instant that OP compounds are detected. However, the instant inventor additionally contemplates that the light source and detector might be maintained separately from the detection surface, with identifying tests being conducted at some central location such as a testing station or laboratory.

In another preferred detection scheme, a biochemically active solid-state layer of AChE is deposited on a microscope slide. After exposure to an unknown compound, the slide is read via spectroscopy, not by shining light onto the face of the slide, but rather preferably by "injecting" light into the glass slide containing the AChE through an edge of the slide. The effect of such delivery is that the incident light beam is reflected internally off of each parallel surface of the slide. Additionally, as is well known to those of ordinary skill in the art, the internally reflected beam extends about ¼ wavelength (e.g., 100–200 nm depending on the wavelength of the incident light) into the surrounding medium through the creation of evanescent light waves. The evanescent light waves penetrate the detector layer on the surface of the slide and interact with the chemicals present thereon. As described previously, the intensity of light that has interacted with the detecting layer is then examined at at least two different spectral wavelengths for evidence of the presence of an OP compound. Preferably, the light that is supplied to the preferred slide embodiment, and which is the source of the evanescent waves, will be delivered by way of optical fibers.

Among the many agents/analytes which are believed to be detectable by the instant invention are "simulants" of chemical and biological warfare agents: DIMP, DMMP, MPA, malathion, parathion and tetracain to simulate organophosphate agents such as Sarin or VX; and imidazole, methionine, thiodiethanol, cysteine, and other sulfur-containing organic molecules to simulate mustards.

In summary, the primary objectives of the instant invention are three fold. First, to utilize the spectral changes of colorimetric indicators such as porphyrins to identify chemical/biological agents (or simulants thereof) at different concentrations. In the preferred embodiment, the colorimetric indicator will either be a porphyrin in solution or a porphyrin immobilized onto a solid surface for use in test aqueous samples and samples in air.

A second object of the instant invention is to exploit the conformational changes in acetylcholine esterase and related enzymes induced by binding of inhibitors, including nerve agents, through the monitoring of spectral changes of colorimetric indicators reflective of that change. A third object of the instant invention is to utilize changes in the spectrographic properties of a reversible competitive inhibitor as a detector for OP and similar compounds.

The foregoing has outlined in broad terms the more important features of the invention disclosed herein so that the detailed description that follows may be more clearly understood, and so that the contribution of the instant inventor to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Finally, it should be understood that the phraseology and terminology employed herein are for the purpose of description and should not be regarded as limiting, unless the specification specifically so limits the invention.

BRIEF DESCRIPTION OF THE DRAWINGS

FIG. 8 schematically illustrates the conformational changes that occur in acetylcholinesterase in the presence of an inhibitor such as VX nerve gas.

DETAILED DESCRIPTION

Figure 1:
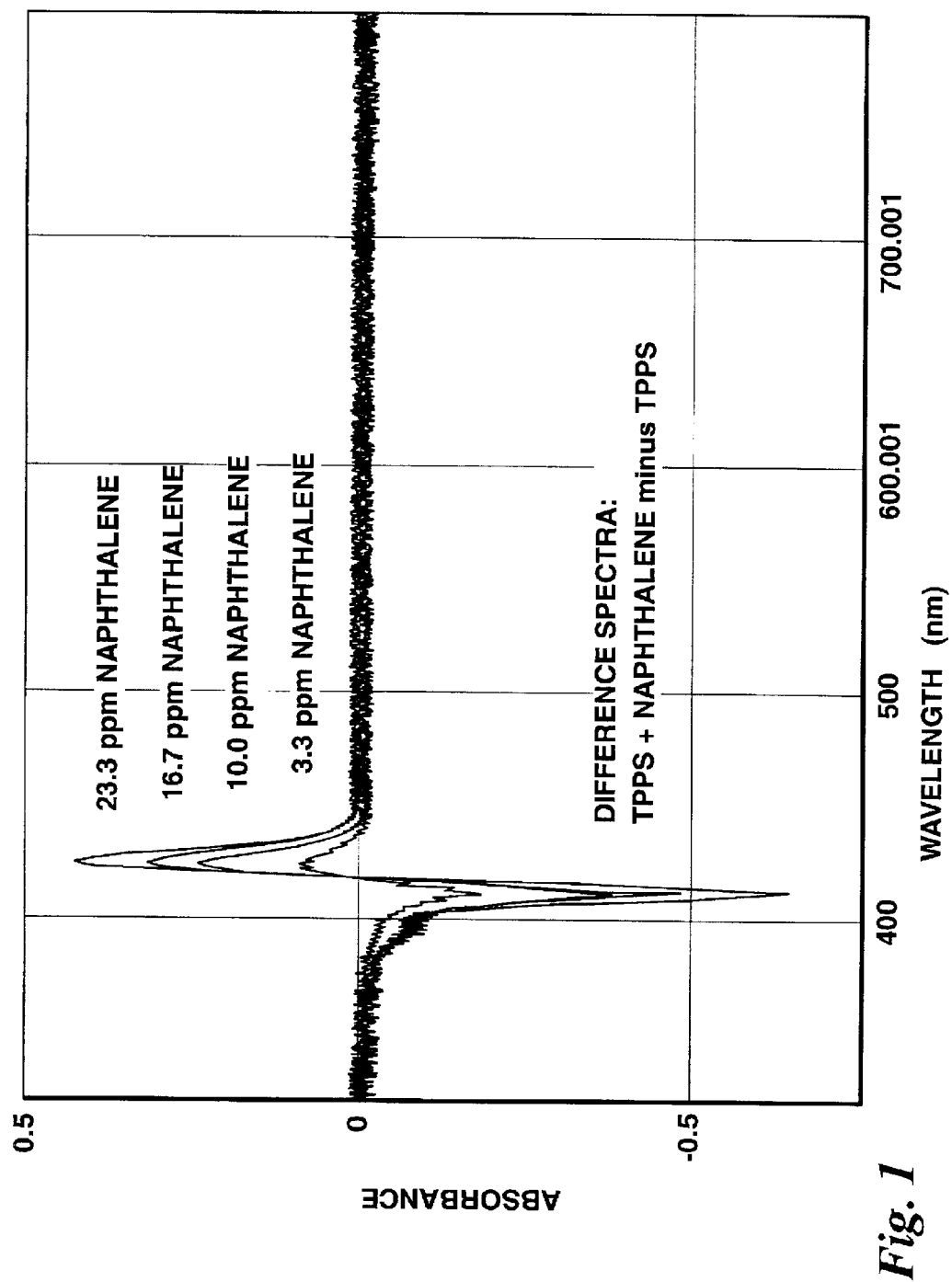
FIG. 1 contains difference spectra of TPPS plus naphthalene minus TPPS for four different concentrations of naphthalene.

The instant disclosure teaches a new approach to the detection of OP-type compounds that are commonly used as warfare (nerve) agents and are also found in some pesticides, etc. The method and apparatus of the instant invention can be configured to detect multiple analytes (such as organic compounds) in liquid or vapor (air) and operates generally by monitoring the optical properties of a chemical that is altered by interaction with the OP/agent. In more particular, analytes can be detected by monitoring changes in the optical properties of the absorbance, reflectance, and/or fluorescence spectra of highly colored heterocyclic compounds such as porphyrins or related compounds such as phthalocyanines. Further, the instant apparatus and method is unique in that it does not require pre-use "calibration" of the colorimetric materials or apparatus. Because the instant invention continuously monitors the detecting surface/volume and compares its spectrographic properties with those of the detecting surface a few moments before, the invention disclosed herein is to a large extent self-calibrating.

A fundamental concept underlying the preferred sensor design is the change in the 3-dimensional conformation of a protein/enzyme when it binds its substrate or specific inhibitor. The binding of substrates to enzyme results in the formation of an enzyme-substrate complex (ES complex) that has been observed to alter the physical shape of the protein as well as the optical spectrum of the enzyme. It is this change in the optical spectrum that is most important for purposes of the instant invention.

General Environment of the Instant Invention

OP compounds inhibit the enzyme acetylcholinesterase, which breaks the neurotransmitter acetylcholine into acetate and choline, by binding at the active site in place of acetylcholine. The phosphate group of the OP agents binds irreversibly with serine (residue #200) in the active site. It is the presence of the serine in the active site of acetylcholine esterase (AChE) as well as trypsin and chymotrypsin, papain, and other enzymes that puts these enzymes in the broad category of "serine proteases or esterases". It is to be expected, and has been observed, that the inhibitor paraoxon—which binds in the same place as acetylcholine—operates to make the overall shape of AChE less ellipsoid. Igarashi, S. and Yotsuyanagi, T. (1993), Analytica Chimica Acta. 281, 347–351. In other words, a conformational change occurs upon binding of an inhibitor (and most likely the substrate as well).

Two specific examples of bindings that result in conformational changes are the joining of oxygen to a crystal of hemoglobin (Hb) and to hemeproteins. First, the binding of oxygen to a crystal of hemoglobin (Hb) results in cracking of the hemoglobin crystal. The wavelength of native deoxy-forms of hemoglobin or myoglobin (Mb) is 430 nm; when oxygen binds, the wavelength maximum (wavelength at which maximum absorbance is observed) shifts to 417 nm. Table 1 shows the wavelength maxima of Mb/Hb with other molecules that resemble oxygen and bind to Hb/Mb in place of oxygen. These molecules act as competitive inhibitors by binding at the active site of the enzyme in place of the substrate. Since the active site is occupied by another molecule, it cannot bind to or catalyze the reaction with the substrate. A similar complex is seen in other (endogenously colored) hemeproteins such as the enzyme cytochrome oxidase in mitochondria where the binding of the natural substrate (again oxygen) changes the wavelength maximum of the oxidase from 444 to 430 nm. Similar shifts are seen when CO binds in place of oxygen; the wavelength maxima at 448 and 604 nm for the reduced form shift to 430 and 590 nm respectively.

TABLE 1

Changes in Wavelength of Hemoglobin/Myoglobin in the Presence of Ligands

| Protein and ligand | B-band | α-band |
| --- | --- | --- |
| Hemoglobin/myoglobin | 430 nm | 555 nm |
| Oxymyoglobin | 417 | 581 |
| Oxyhemoglobin | 415 | 577 |
| CO-hemoglobin | 419 | 568 |
| Methemoblobin (oxidized with bound water) | 406 | 630 |

Binding of an inhibitor to a site other than the active site can also result in changes in the conformation of a protein enzyme. This sort of binding would characterize a non-competitive inhibitor, which is one that does not compete with substrate for the active site. For example, 2,3-diphosphoglycerate binds to deoxyhemoglobin at the center of symmetry of the tetramer consisting of 2 alpha and 2 beta chains in a central cavity far removed from the oxygen-binding (heme) sites and stabilizes the deoxyhemoglobin T-form quaternary structure by cross-linking the B-chains. The T-form is less compact than the R-form (oxygenated), a clear example of a conformational change induced by a non-competitive inhibitor.

Similarly, binding of glycyltyrosine, a slowly hydrolyzed substrate of the enzyme carboxypeptidase A, results in a large conformational shift in the active site configuration. During the binding, tyrosine-248 moves from the surface to the active site. This closes the active site and converts it from a hydrophilic to a hydrophobic region. Other significant changes in conformation are also observed.

Conformation of the protein can be determined several ways: the change in size or shape of the protein can be measured by alteration of its passage through a porous sieve (such as Sephadex); by changes in the rate of electrophoretic migration through a meshwork in an electrical field; optical measurement of changes in circular dichroism (CD) or optical rotatory dispersion (ORD) due to changes in alpha-helix and beta sheet regions of the protein. Changes in conformation can also be detected by changes in the fluorescence/absorbance of a "reporter" molecule such as anilinonaphthalene sulfonate (ANS) or a molecule whose optical characteristics are affected by its environment.

One class of molecule whose optical characteristics are altered by the presence of other molecules including proteins—and which is of particular importance for purposes of the instant disclosure—is the porphyrins. As will be shown hereinafter, the spectra of porphyrins is altered by the presence of numerous organic compounds (e.g., naphthalene, benzene, formaldehyde, isopropanol, alcohols, amino acids, nucleic acids, etc.) including proteins at micromolar or lower concentrations. Thus, porphyrins or similar molecules are the preferred colorimetric indicator of nerve-agents-induced conformational changes for use with the instant invention.

Spectral Properties of Porphyrins

One explanation for the observed spectral changes in the porphyrins is the alteration of pi-electrons of the porphyrins (this gives them their intense color) by the analyte molecules. Because of the spectral alterations due to amino acids, changes in the absorbance spectrum of porphyrins by proteins (made up of amino acid residues) are both expected and observed in practice. An example of this change in the porphyrin spectrum is shown in FIG. 1, where the wavelength maximum of tetraphenylporphyrin sulfonate (TPPS) changes from 413 nm to 426 nm in the presence of naphthalene, indicated by a decrease in absorbance at approximately 413 nm as TPPS is changed into the naphthalene-TPPS adduct absorbing at 426 nm; in these spectra the difference spectrum is shown in which the spectrum of TPPS alone is subtracted from the spectrum of TPPS in the presence of naphthalene. Shifts in wavelength maxima are observed with different analytes in either free aqueous or immobilized TPPS in either water or air medium. Some examples are given in Table 2.

TABLE 2

Changes in Soret Absorbance of TPPS in Presence of Analytes

| ANALYTE | Absorbance decrease at (nm) | Absorbance increase (nm) | Immobilized | Medium |
| --- | --- | --- | --- | --- |
| Isopropanol | 431 | 421 | yes | air |
| acetone | 434 | 423 | yes | air |
| methanol | 429 | 418 | yes | air |
| formaldehyde | 431 | 421 | yes | air |
| ethanol | 427 | 416 | yes | air |
| naphthalene | 413 | 426 | no | $H_2O$ |
| benzene | 413 | 419 | no | $H_2O$ |
| formaldehyde | 413 | 434 | no | $H_2O$ |
| naphthalene | 424 | 422 | yes | $H_2O$ |
| tyrosine | 413 | 423 | no | $H_2O$ |
| tryptophan | 413 | 425 | no | $H_2O$ |
| glycine | 409/415 split | no peak | no | $H_2O$ |
| methionine | no loss | 413 | no | $H_2O$ |
| adenine | 411 | 421 | no | $H_2O$ |
| thymine | 411 | no peak | no | $H_2O$ |

Changes in the Q- (alpha) bands not listed here.
The shift in wavelength maximum is also different for different proteins, as shown in Table 3.

TABLE 3

Change in Wavelength of soluble TPPS by Proteins

| Protein | Wavelength of TPPS-protein Complex |
| --- | --- |
| RNAase | 425 nm |
| albumins | 422 |
| trypsin | 421.5 |
| glucosidase | 420 |
| acetylcholine esterase | 424 |
| lysozyme | 426 |

Figure 2:
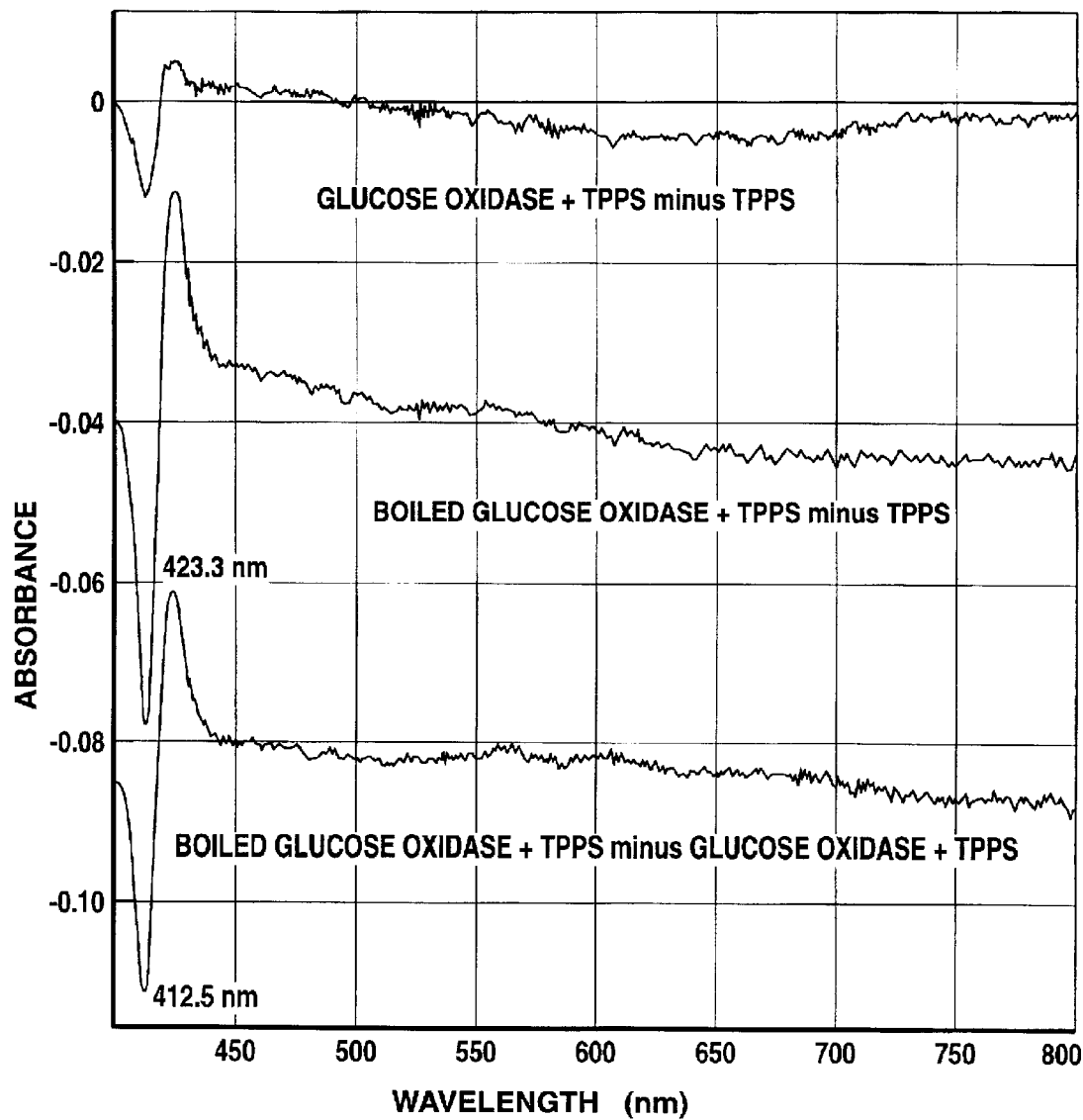
FIG. 2 illustrates difference spectra of glucose oxidase, boiled glucose oxidase, and boiled glucose oxidase minus glucose oxidase all in the presence of the porphyrin TPPS.

Boiling a protein "denatures" it, changing its "natural" structure, just as frying an egg denatures the protein as witnessed by a change in the nature of the white and the yolk. As seen in FIG. 2, boiling denatures glucose oxidase. In the presence of normal glucose oxidase, only a small decrease in absorbance at 412.5 nm is observed. In the presence of boiled glucose oxidase, the absorbance decrease at 412.5 nm is larger and a new absorbance peak at 423 nm is observed (not observed in "normal" glucose oxidase). If TPPS were to experience the same environments in boiled as in native glucose oxidase, there would be no difference in the spectra of boiled and native protein. A change in spectrum indicates that the porphyrin TPPS reflects the change in conformation of the protein caused by boiling.

Porphyrin Properties

Porphyrins are nitrogen-containing compounds that are derived from the parent molecule tetrapyrroleporphin and which are very useful for purposes of the instant invention. They are classified on the basis of the nature of the side chains replacing the hydrogens at positions 1–8; methyl, ethyl, vinyl, and propionic acid are common substituents.

Complexation of porphyrins with metal alters the absorbance spectrum of the porphyrins. It is of interest to note that the wavelength is dependent on the metal as well as the solvent used. In a given solvent, the wavelength maxima of the different metal complexes are sufficiently different to allow spectrophotometric resolution of the different metal complexes. The absorbance spectrum and the extinction coefficient (absorptivity) of a metallo-/porphyrins are known to be affected by the solvent. The basis for these solvent-induced spectral changes is similar to the basis of the change in the wavelengths absorbed by altering the groups substituting at positions 1–8 on the porphyrin ring. Factors which cause an increase in pi-electron orbitals at the periphery of the porphyrin tend to cause red shifts of the absorbance and fluorescence (if present) bands. Red shifts are found to arise as a function of the electron affinity of side chain substituents at positions 1–8. As the electronegativity is increased, the stability of the metal chelate decreases and absorption/emission bands shift accordingly. As pi electrons are withdrawn from the periphery, the spectrum blue shifts to shorter wavelengths.

Just as the energy transitions for absorbance of photon energy are altered, so are the energy transitions involved in photon emission of absorbed energy. Thus the fluorescence spectra of porphyrins is altered, each having its unique spectrum.

Detection of Organic Ligands by Complex Formation with Porphyrins

As a threshold matter, in order to function as a detector for purposes of the instant invention, the detector molecule must be able to interact with the target analyte(s) and its spectrum (absorbance, fluorescence, or reflectance) must be altered by the interaction. In the preferred embodiment, and for reasons set out in more detail below, porphyrins, when combined with AChE, are especially suitable for use as the detector component of the instant invention.

A number of publications report the chemical alteration of organic molecules by the catalytic activity of porphyrins and porphyrin-like heterocyclic compounds. In view of the intense light absorbance by these molecules, some of the catalytic processes are light-activated and light-dependent; others may require the presence of a reductant as well.

Of particular importance for purposes of the instant invention are the spectrographic changes that occur in porphyrin catalyzed reactions. The crux of the phenomenon is that in order for porphyrins to catalyze an organic reaction, the porphyrin must bind, "dock" with, or somehow interact physically with the organic at least once during the catalytic process (a collisional encounter between substrate and catalyst). In those cases where a reactant [such as $OH^-$, $H^+$, electrons, $O_2^-$, $^1\Delta_g O_2$ (singlet oxygen)] may be generated at the porphyrin and difuse to the organic molecule, the diffusion distance must be very small (the lifetime of singlet oxygen in $H_2O$ being on the order of nanoseconds), indicating that the porphyrin and organic are very close together, probably "docked".

Docking of the organic, analogous to the formation of an enzyme-substrate complex, should result in a distortion of the electron distribution of both molecules. Since the pi-electron distribution of the porphyrins is responsible for their intense visible light absorbance, alterations of porphyrin spectra upon organic ligation should be seen. This idea is consistent with the changes in $\epsilon$ and $\lambda_{max}$ of the Soret (400–450 nm) band (B-band) of the porphyrins by alteration of the porphyrin side chain constituents of the porphyrin ring, as shown in FIG. 1 and Table 2, and alteration of the spectral properties due to solvent polarity and hence differences in the electron distribution around the porphyrin plane (cf. Table 2).

Alteration of the spectrophotometric characteristics of porphyrins has been reported by, for example, D. Mauzerall (Biochem. 4, 1801–1810, 1965) and J. A. Shelnutt, J. A., (J. of Phys. Chem. 87, 605–616, 1983), the disclosures of which are incorporated herein by reference. In these studies aromatic heterocyclic compounds such as phenanthrolines were complexed with porphyrin molecules; changes in pi-orbital density were observed, leading to changes in visible light absorbance, fluorescence, and Raman spectra.

Close interaction of porphyrins and organics resulting in the quenching of porphyrin absorbance and fluorescence spectra have been reported. Further, porphyrins have been used in the shape-selective separation of aromatics and are particularly useful in the separation of fullerenes. Soret $\lambda_{max}$ positions have been observed to change in the presence of organic polycyclics, the shift in $\lambda_{max}$ being proportional to the energy of association with the porphyrin. This suggests that the stronger the interaction between organic and porphyrin, the greater the shift in wavelength.

The use of porphyrins and phthalocyanines as chemical sensor indicators is gaining in popularity. Wavelength shifts as colorimetric indicators have been used to sense the presence of pentachlorophenol, cysteine and histidine, and quinones. The binding of the quinone has been determined to be via multiple H-bonds between the quinone and the OH-naphthyl subgroups of the porphyrin as well as between the quinone and the COO$^-$ groups of Zn- porphyrin dinitrobenzoic acid. A gas sensor which measures CO, $NO_2$, and $H_2S$ has been designed using metalloporphrin Langmuir-Blodgett films deposited on a field-effect transistor. Dziri, L., Bousaad, S., Tao, N. and, Leblanc, R. M. (1998) Langmuir 14, 4853–4859.

In related work, the photo-induced energy transfer between two porphyrins which have been co-deposited as solid film on $TiO_2$ has been measured, indicating the ability of energy transfer between porphyrins and their near (docked) neighbor. Illumination of a donor molecule elicits energy changes in the acceptor porphyrin although no electron transfer occurred, indicating that changes in one molecule elicit spectral changes in another neighboring acceptor molecule. This is similar to the recognition of specific DNA sequences using oligonucleotide-derivatized polypyrroles by voltammetry and the interaction of porphyrin-thymidine complex with DNA in which the H-bonding of the porphyryl-thymidine with adenine results in an 8 nm red shift in the porphyrin Soret band.

Thus, alteration in the electron density due to interaction and/or binding with another molecule, even at the periphery of then porphyrin, results in spectroscopic changes. This is the physical basis of our porphyrin-based sensor system.

Detection of Organic Ligands via Reversible Competitive Inhibitors

According to another preferred embodiment, there is provided a real-time detector of OP, and other similar compounds, that utilizes a reversible competitive inhibitor in combination with spectrographic analysis of at least two different light wavelengths. By way of summary, in the preferred embodiment a detector is formed by depositing a biochemically active solid-state layer of AChE on a microscope slide as is described below. As a next preferred step, a porphyrin is bound at the active site of the AChE molecule, which porphyrin is chosen so as to bind weakly to AChE and, thus, be subject to displacement by OP compounds. Exposure of the AChE/porphyrin detector to OP or similar compounds will result in the porphyrin being displaced from its location at the active site, thereby resulting in a change in the spectrographic properties of the detector. As has been discussed previously, the instant invention preferably utilizes real-time spectrographic measurements at light wavelengths of about 405 and 426 nm in order to determine whether or not the porphyrin has been displaced and, hence, whether or not OP compounds are present in the sample.

Turning now to a discussion of this aspect of the invention in more detail, as a first step, microscope slides are obtained that have been coated with amino groups. Slides sold under the trademark "Probe-On" from the company "Fisher Scientific" are particularly suitable for this purpose. Alternatively, a plain glass slide might be prepared by treating it with a chemical such as 3-aminopropyltriethoxy silane, which would "functionalize" its surfaces and result in free amino groups that are bound thereto. It should be noted that a glass slide is only a preferred choice and, as is described more fully below, plastic, silica, quartz, plexiglass, or many other materials might be used instead. Preferably, and for ease in later evaluating the detector, the material on which the amino groups are found will be optically transparent.

Given a coated microscope slide as described previously, the amino groups present thereon are then preferably reacted with glutaraldehyde to form a Schiff's base, which can then be used to bind a preferred dendrimer which is sold under the trademark "Starburst" by Aldrich Chemical. The trademarked dendrimer is preferred because it has 64 amino termini, which effectively amplifies the number of binding sites by a factor of 64. The 64 amino sites are then reacted with glutaraldehyde to form a Schiff's base and then acetylcholineesterase or the desired enzyme is bound. Therefore, the net result is a layer of enzyme that is covalently bound to the glass, in effect, a "sandwich" of glass/Starburst/acetylcholineesterase (or other proteins). In a preferred arrangement, as a next step the porphyrin is attached to the AChE by preparing a 70 micromolar solution of porphyrin in 75% ethanol and placing that mixture on the slide for about 15 minutes, after which the slide is washed and is ready for use as a detector.

Thus, if the above-described AChE detector, i.e., one with a suitable porphyrin bound at the active site, is exposed to OP or similar compounds, the OP compounds will react with the detector material and the attached porphyrin will be displaced (i.e., it is a reversible inhibitor). Since, the porphyrin is not strongly bound, it is easily displaced from its position, thereby providing a means for recognizing when OP and similar chemicals are present. Of course, when the porphyrin is displaced, the spectrum of the biosensor changes again.

For purposes of detection, the spectrum of the AChE/porphyrin complex will preferably have been determined in advance of its exposure to an unknown, especially at the 405 nm and 426 nm wavelengths. These spectral values can be used as baseline values and compared with the spectral values after/during exposure to check for OP compounds. Later, when an inhibitor binds with the complex on the detector, it will displace the poorly bound porphyrin. Evidence of this displacement will be manifest in from an increase in the 405 nm spectral band will and a decrease in the 426 nm band. Those of ordinary skill in the art will recognize that the specificity of the detection method suggested herein is twofold. First, only those molecules that are specific inhibitors of the enzyme will bind and displace the porphyrin. And, second, the spectral wavelengths that are monitored are specific for the particular porphyrin used.

As will be further recognized by those of ordinary skill in the art, the use of a competitive inhibitor such as that described above will result in a porphyrin that weakly binds at the same site on the AChE molecule that the substrate acetylcholine, nerve gasses, organophospates, and other inhibitors bind. Additionally, when the porphyrin binds to AChE, a marked change in the spectrum of the porphyrin is observed, since the porphyrin now "senses" the environment of the active site of the AChE. Finally, the weakly-bound porphyrin is readily displaced from its location on the active site either by substrate (acetylcholine) or other inhibitor whose binding site is also at the active site since (hence making it a reversible inhibitor). When the porphyrin molecule is displaced, the spectrum of the biosensor will change, which change can then be detected via spectrographic analysis as discussed previously.

In conclusion, $TPPS_1$ is an effective competitive inhibitor of AChE causing a reversible inhibition. Specific spectral changes at the 402 nm and 442 nm wavelengths occur in the $TPPS_1$ absorbance spectrum when the porphyrin binds to AChE. The spectrum of the $TPPS_1$-AChE complex can be altered in the 442 nm region by addition of compounds which bind at the active site of AChE, such as AChI and tetracaine, and not those which bind elsewhere (procaine).

Although the detector described above could be read via conventional reflectance or absorption spectroscopy, because of the low concentration of the reagents thereon, an alternative method of assessment is preferred. Thus, and according to another aspect of the instant invention, there is provided a method of reading the above-described detector via spectroscopy which is performed by "injecting" light into the slide upon which the AChE is bound through one of its edges, thereby creating evanescent waves which are then utilized to read the detector.

By way of general background, it is well known to those skilled in the art, that when light is incident on a medium at an angle of incidence that is greater than the critical angle, Snell's law suggests that all of the light will be reflected internally at that interface, i.e., total internal reflection will occur. However, Fresnel's equations (in concert with Maxwell's equations) predict—and, in fact, it is observed in practice—that evanescent waves will be generated at the point of total reflection. The energy of this type of wave penetrates beyond the surface of the reflecting medium and returns to its original medium unless a second medium is introduced into the region of penetration of the evanescent wave. In other words, if another medium is brought near enough to the point where total internal reflection occurs, energy in the form of evanescent waves of the same frequency as the incident light will be transmitted to the alternative medium.

Of course, if molecules are brought into proximity with a surface in which evanescent waves are propagating, the molecules will interact with those waves and attenuate them to the extent that these molecules would absorb the same wavelength in conventional light, i.e., in absorption spectroscopy. Spectroscopy via evanescent waves is a well known method of assessing the composition of low concentration materials, such as those which would be present in the preferred embodiment of the instant invention.

Turning now to the preferred embodiment of the instant invention, the evanescent waves typically extend about ¼ wavelength (e.g., 100–200 nm depending on the wavelength of the incident light) into the surrounding medium. The evanescent light waves penetrate the detector layer on the surface of the slide and interact with the chemicals present thereon. As described previously, the intensity of light that has interacted with the detecting layer is then examined at at least two different spectral wavelengths for evidence of the presence of an OP compound, e.g., at 405 nm and at 426 nm.

Preferably, the light that is supplied to the preferred slide embodiment, and which is the source of the evanescent waves, will be delivered to the detector by way of optical fibers according to methods well known to those of ordinary skill in the art.

Finally, as has been discussed previously, in the preferred embodiment the instant detector will be created on glass or similar material that is optically transparent. In light of the foregoing, it should now be clear why this arrangement is preferred, as it provides a convenient way to generate and use evanescent waves when detector materials are read. Of course, preferably the glass, plexiglas, etc., will be of a density, thickness, and configuration to encourage generation of such waves. For example, although thin planar pieces of transparent material such as microscope slides are preferred, sections of fiber optic cable which have been treated as described previously could alternatively be used.

Experimental Results

The majority of the data described hereinafter were obtained using a member of the class of heterocyclic compounds called the porphyrins discussed previously, the water soluble tetraphenylporphyrin sulfonic acid (TPPS). The spectrum of a typical porphyrin consists of an intense highly absorbing "Soret" or B-band in the 400–450 nm region and less intense Q-bands in the 500–700 nm (visible light) region. Bands in the UV and NIR are present as well, and the porphyrins exhibit intense fluorescence.

There are several lines of experimental evidence that clearly indicate that alteration of the UV-VIS spectra of porphyrins takes place as a result of interaction with other (electron distorting) organics. For example, immobilization of porphyrins at a high density on a surface results in red-shifted peaks and decreased $\epsilon$ (absorptivity or extinction coefficient) due to ordered stacking of porphyrins such that the porphyrin plane is perpendicular to the surface. Additionally, the spectrum of free or (covalently or electrostatically) immobilized TPPS is altered by the presence of various chemicals including:

A) Naphthalene. FIG. 1 shows the spectra of TPPS immobilized on dialysis tubing (cellulose) in the presence/absence of naphthalene. Ligation of naphthalene causes a concentration-dependent loss in 412 nm absorbance (loss of TPPS) and an increase in 426 nm absorbance caused by the formation of a TPPS-naphthalene complex. Wavelength maxima changes are also observed in the Q-bands (500–700 nm). The absorbance changes are linear with the concentration of naphthalene present and indicates that concentrations equal to or less than 1 ppm (1.7 mM) naphthalene can be detected.

B) Benzene. Complexation of soluble TPPS with benzene causes a loss of 413 nm absorbance (TPPS loss) and an increase in 419 nm as TPPS is converted to a benzene-TPPS complex in a concentration-dependent manner. In addition, the Q-bands (500–700 nm) of TPPS in the presence of benzene are located at 517, 550, 588, and 646 nm compared to 517, 553, 578, and 635 nm in the absence of benzene.

The spectral changes induced by the presence of naphthalene are not the same as those induced by benzene. The difference spectra of organic+TPPS minus TPPS are very different for benzene and naphthalene. This indicates that organics can be distinguished from one another on the basis of their effect at all five (B and Q) absorbance bands. Each organic has its own spectral signature.

C) Amino Acids. The spectrum of TPPS is altered by the presence of methionine (known to bind porphyrins) and tyrosine, tryptophan, and glycine as representative amino acids. Different unique patterns of the B- and Q-spectra (wavelength shifts and changes in intensity) are observed for each of the 20 amino acids.

D) Proteins also induce unique spectral changes in TPPS as shown in Table 3 presented previously. In the presence of the protein, a new wavelength given below is observed.

Finally, solid state immobilized porphyrin films can be used to detect the presence of aromatic analytes (organics) in air. To demonstrate this statement, difference spectra may be obtained by first recording the spectrum of the unreacted TPPS film. A small amount (about 10 μl) of liquid analyte (methanol, ethanol, etc) can then be added to the chamber and then the spectrum of the film again recorded at different time intervals. The spectrum of the unreacted film is then subtracted from the reacted film to show the change in the spectrum due to exposure to the analyte.

Specificity

As shown in Table 2, the changes in the spectrum are fairly specific for the analytes used. The utility of the porphyrins and related indicators lies in the presence of multiple absorbance bands and the fact that an analyte affects each of the five bands differently. This is clearly indicated in the difference spectra of isopropanol and formaldehyde. While all analytes result in an increase in absorbance at 421 nm and a decrease at 431 nm (immobilized TPPS has it $\lambda_{max}$ at 431 nm), formaldehyde shows an increase in absorbance centered at 513 nm while isopropanol shows an increase at 519 nm and noticeable increases at around 550 and 580 nm. Changes at 550 and 580 nm are not as noticeable in the presence of formaldehyde.

Table 2 illustrates the great selectivity and specificity of analyte detection due to the increase in absorbance due to complex formation in the Soret. It is apparent that some analyte-porphyrin complexes have similar wavelengths in the Soret band. However, when absorbance as well as wavelength differences at the Soret and the Q-bands is recorded, each analyte is different.

If an indicator (such as porphyrin) with five bands is available and it is assumed that the wavelength in each band can either increase, decrease, or stay the same, and, further, that the intensity at each band can either increase, decrease, or stay the same, then there are $5^6$ or over 7700 possible permutations of these factors. If the magnitude of wavelength shift or absorbance changes is specified (again each band is independent of the others), the number of potentially-detectable analytes increases dramatically.

The key to obtaining specificity is to use data from as many absorbance bands as possible. Small changes in wavelength or intensity are easily detected in the difference spectrum, which is discussed in below. Most analytes present a unique "signature" when all available absorbance bands are considered. An indicator with only one absorbance band has very limited utility.

Sensitivity

A primary requirement for effective detection of hazardous agents is that the apparatus and method be able to detect (very) low levels of hazardous agents. Not unexpectedly, the absorbance changes that would be expected at low concentrations are rather small. However, increased sensitivity of a detector formed according to the instant invention can be potentially achieved by several means. For example, different porphyrins, phthalocyanines, or indicators with higher extinction coefficients can be used. Alternatively, it is well know that, generally speaking fluorescence is a more sensitive tool than absorbance, typically by an order of magnitude or so (although the fluorescence bands are very broad compared to absorbance). Thus, a small detector incorporating absorbance as well as fluorescence could increase the sensitivity of the.

Finally, increased sensitivity may be obtained by matching a particular porphyrin to the specific agent that is sought. Since the effective sensitivity is related to the extinction coefficient of the indicator used, it is possible that it might be necessary to construct "designer" porphyrins with sidechain substitutions specific for a single analyte (much like specific antibodies but with five absorbance bands).

The Difference Spectrum

Consider the following simple illustration. If it is assumed that an analyte shifts the $\lambda_{max}$ of a porphyrin from 413 to 429 nm, for example, the quantitation of the analyte from the absolute spectrum of the porphyrin and analyte will require that at least 10–20% of the porphyrin be complexed. So, if 5 mmoles of porphyrin are present on an active detector surface, then 1 mmole of analyte must bind before the effect can be directly seen in the spectrum of the porphyrin. Further, the smaller the wavelength shift, the less sensitive the quantitation and the more analyte complex must be present to be measured. Thus, detection of low concentration compounds poses a significant challenge to analytical methods that are based on direct measurement and observation of the spectrum.

Hence, the instant inventor has determined that it is preferable that, rather than attempting to directly detect the presence of analyte in the spectrum of the porphyrin, a mathematical operation should be performed on the spectrum to make clearer the change in that takes place when an analyte is introduced into the system of the instant invention. That is, a central precept of the instant invention is that the preferred method of identifying low concentration compounds is to "continuously" monitor the detector compound and to continuously compare the current spectrum with a spectrum collected at some previous time. By comparing the spectrum at two different points in time, a self-calibrating procedure is developed that is much more sensitive than other approaches considered heretofore.

According to a first preferred embodiment, the instant method is made more sensitive to low levels of analyte by utilizing a difference spectrum, where the spectrum of unreacted porphyrin (or other colorimetric compound) is subtracted from its spectrum following exposure to the analyte. As shown in FIG. 1, the difference spectrum—which is computed by subtracting the spectrum of TPPS alone from the spectrum of TPPS+naphthalene—resembles a "1st derivative" function. The absorbance at 413 nm decreases due to loss of TPPS when naphthalene binds and shifts the wavelength (new peak) to 419 nm. Knowing the extinction coefficient of TPPS at 413 nm allows the determination of how much TPPS is lost; this is the same amount of TPPS-naphthalene complex formed.

The presence of low levels of analyte is virtually undetectable except by monitoring the change in the spectral characteristics of the detector. Unlike absolute spectra where the shape and peak wavelength of the spectral curve changes with increasing binding of analyte, the $\lambda_{max}$ and $l_{min}$ do not change; only the absorbance changes with changes in analyte concentration. For example, in the presence of increasing benzene, the Soret absorbance band shows only small shifts to longer wavelengths since the Soret in the presence of benzene is a combination of the TPPS peak at 413 nm and the TPPS-benzene peak at 419 nm. The difference spectrum of these two spectra clearly reveals the loss of absorbance at 413 and the increase at 419 nm due to benzene complexation of only some of the TPPS present. The combination of these 2 absorbance bands results in the small wavelength shift.

The magnitude of the wavelength shift will not alter the sensitivity of the difference spectrum. The closer the wavelengths of the porphyrin and porphyrin-analyte complex, the sharper the "1st derivative" appearance of the difference spectrum and the more the change in absorbance analyte concentration. The farther apart the wavelengths, the broader the peak and trough of the difference spectrum. In all cases, the integrated area under the curve will always be proportional to analyte concentration.

It is important to note that the use of difference spectra to detect an analyte-indicator complex also means that the sensor and active surface do not need to be calibrated prior to use and that a partially-used sensor is still completely useful. This is so because, first, it is the time-dependent change in absorbance and not the absolute amount of indicator that is monitored. The loss of TPPS or other indicator, for example, can be quantitated from its extinction coefficient, the absorbance loss being proportional to the amount of porphyrin which reacts with analyte.

Second, since difference (comparison) spectra are used, a spectrum recorded at any previous time can be subtracted from the current spectrum to yield a measure of the change since the earlier reading. For example, the spectrum of the film at some arbitrary zero time could be subtracted from the spectrum five minutes later after exposure to analyte X. To determine if more analyte is present at, say, ten minutes, either the zero or five minute spectra could be subtracted. In the first case (i.e., t=0 subtracted) the total exposure after 10 minutes is measured; in the second case, only the change between t=5 and t=10 minutes is recorded. If in the period between 5 and 10 minutes analyte Y binds which causes an absorbance change at a different wavelength than analyte X, the difference between the zero and ten minute spectra would show a deep trough at the TPPS peak at 413 nm and 2 peaks at the wavelengths corresponding to the TPPS-X and TPPS-Y complexes. The 10 minute minus 5 minute spectrum indicates the amount of TPPS that reacted in the 5 minute period (loss in 413 nm) and the absorbance increase at the $\lambda_{max}$ of the TPPS-Y component without interference by the TPPS-X complex formed previously. In this case, the same film can report multiple analytes. Also, the need to "calibrate" or use a fresh indicator is unnecessary since changes in the absorbance are measured regardless of the original intensity of the indicator.

More generally, it is contemplated by the instant inventor that any number of mathematical comparisons between the spectra and two different time periods could be used to accentuate the change occasioned by the introductions of low concentrations of the target compound. For example, in some cases taking the ratio of corresponding spectral intensities might be useful. In other cases, ratios (or differences, products, etc.) between the squared, cubed, etc., spectral intensities might prove effective. Obviously, many more combinations might be devised by one of ordinary skill in the art. Thus, for purposes of the instant invention, the term "difference" should be interpreted broadly to include any mathematical combination of a spectra intensities at one period of time with corresponding intensities at another period.

Interaction Time

The spectral changes observed in porphyrins are typically completed within approximately 1 second in both soluble (free, aqueous) and immobilized porphyrins. Thus, for detection purposes, spectral measurements might be collected at least this often.

Response to Changing Analyte Levels

Unless it becomes "saturated", any detector will respond to increasing analyte levels. But, it is much less common to find a detector that can respond to decreasing levels of a compound. However, the instant system is one such detector.

Decrease in naphthalene and other aromatic levels in the presence of TPPS can be detected in the instant system by the change in the difference spectrum of analyte plus TPPS minus TPPS. As has been discussed previously, the trough at 413 nm represents the loss of TPPS due to the formation of the naphthalene-TPPS complex observed at 426 nm. Decreasing the naphthalene concentration by allowing naphthalene evaporation from the solution results in a decrease in the "depth" of the trough at 413 nm as the analyte complex dissociates. Thus, the spectrum reflects a decrease as well as an increase in analyte level. The instant inventor has also shown that removal of analytes from the vicinity of immobilized TPPS surfaces can result in a return to the pre-exposure spectrum of TPPS; the analyte can dissociate from the porphyrin, thereby "regenerating" the indicator material.

Using Immobilized Proteins as Detectors

Methods for immobilizing proteins on solid substrate are well known to those of ordinary skill in the art. For example, antibodies and proteins are immobilized onto 96-well ELISA plates either electrostatically or covalently using commercially-available products from Corning Costar or Xenobond (Saddle Brook, N.J.). Affinity columns are routinely made by covalent linkage of proteins to column matrices such as CN—Br activated Sepharose (Pharmacia) and have even been used by this investigator to separate organelles.

Enzymes have been immobilized onto electrode surfaces or films used in their assembly, just as used in a Clark oxygen electrode. As in the case of immobilization for ELISA, preservation of the enzyme structure and catalytic ability is desirable and imparted by the immobilization. Others have immobilized octopine dehydrogenase and pyruvate oxidase to cellulose triacetate (chitosan) using glutaraldehyde to make an octopine sensor (senses Oxygen uptake via Clark electrode); nucleoside phosphorylase and xanthine oxidase to chitosan to make a phosphate, inosine, and hypoxanthine biosensor sensor; and ornithine carbamyl transferase and nucleoside phosphorylase to cellulose triacetate using glutaraldehyde. Still others have immobilized phosphotriesterase (OP hydrolase) to polyurethane polymer using isocyanate cross-linking to generate a protein-filled "sponge" used for nerve gas decontamination form surfaces. It is also possible to immobilize organophosphate hydrolase, acetylcholine esterase, and choline oxidase onto activated silica gel using glutaraldehyde to produce a biosensor to detect OPs like paraoxon; this sensor measures the production of colored product from the breakdown of an analog of acetylcholine. Additionally, it is known that it is possible to cross-link cholinenoxidase and AChE onto a Pt-electrode to fabricate a sensor to detect the OP dichlorvos (dimethyl 2,2'-dichlorovnyl phosphate). In summary, the enzymes affected by OPs can be immobilized and cross-linked in a variety of ways without loss of specificity or activity and with increased stability and active life.

Using Porphyrins to Detect Conformational Changes in Proteins

It is well known that boiling denatures proteins. As seen in FIG. 2, in the presence of native glucose oxidase, only a small decrease in absorbance at 412.5 nm is observed. In the presence of boiled glucose oxidase, the absorbance decrease at 412.5 nm is larger and a new absorbance peak at 423 nm is observed (not observed in "normal" glucose oxidase). If TPPS were to experience the same environments in boiled as in native glucose oxidase, there would be no difference in the spectra. A change in spectrum indicates that the porphyrin TPPS reflects the change in conformation of the protein caused by boiling.

Figure 3:
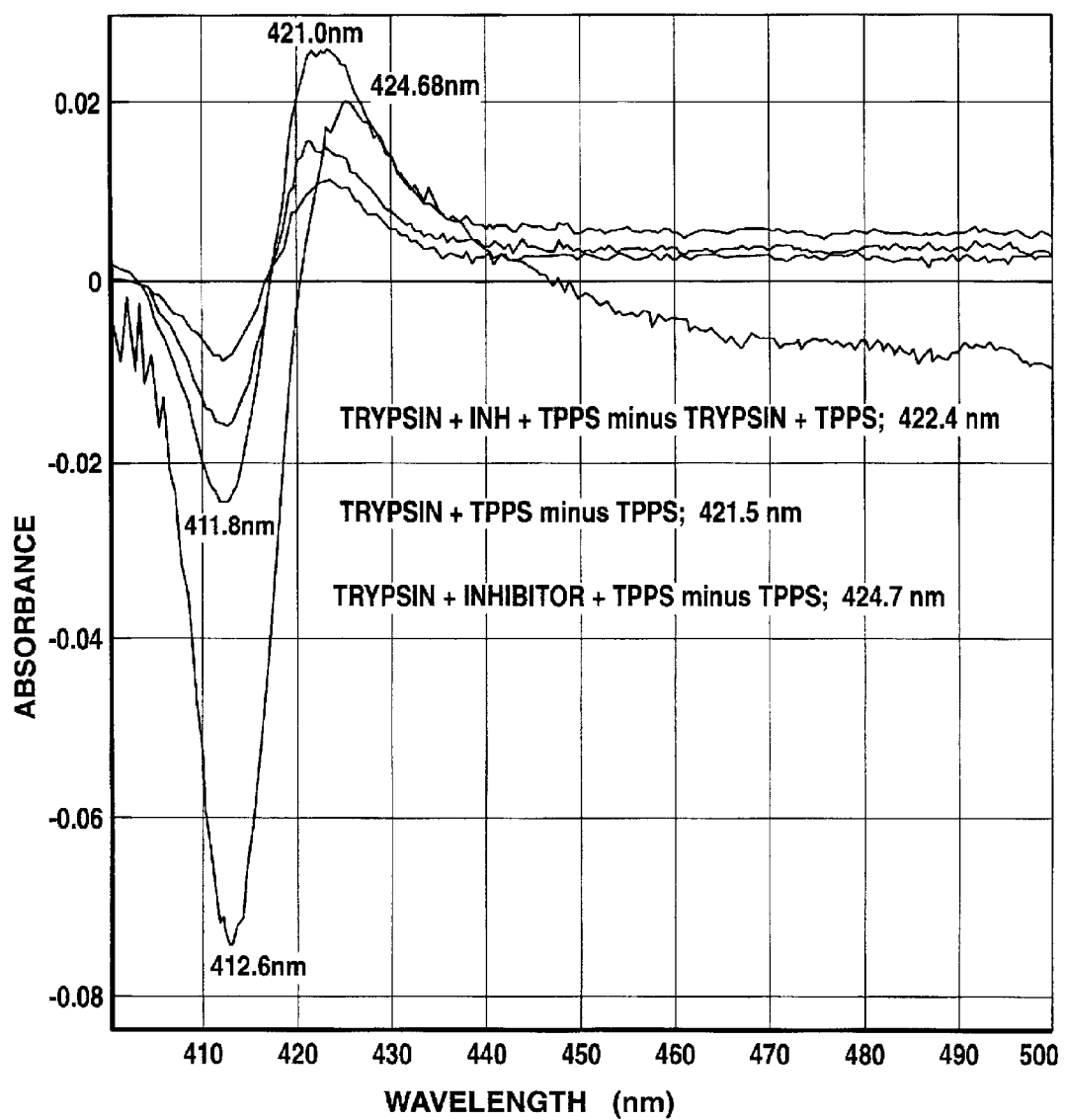
FIG. 3 contains differences spectra of Trypsin plus Inhibitor (INH) plus TPPS minus Trypsin plus TPPS; Trypsin plus TPPS minus TPPS; and, Trypsin plus inhibitor plus TPPS minus TPPS.

Trypsin, like AChE, has a serine at the active site that reacts with substrate. Trypsin is inhibited by a small 6 kilodalton protein that, similar to the action of OP with AChE, binds at the active site and prevents the binding of substrate. The binding of the inhibitor to trypsin alters the spectrum of TPPS, as seen in FIG. 3. Trypsin alone causes a decrease in absorbance at 411.8 nm as TPPS reacts with the protein and absorbs light at a new wavelength 421.5 nm due to interaction of TPPS with a region of the protein. The inhibitor alone causes the appearance of a peak at 424.7 nm. In the presence of both trypsin and its inhibitor, the absorbance increase is seen at 421.9 nm.

Figure 4:
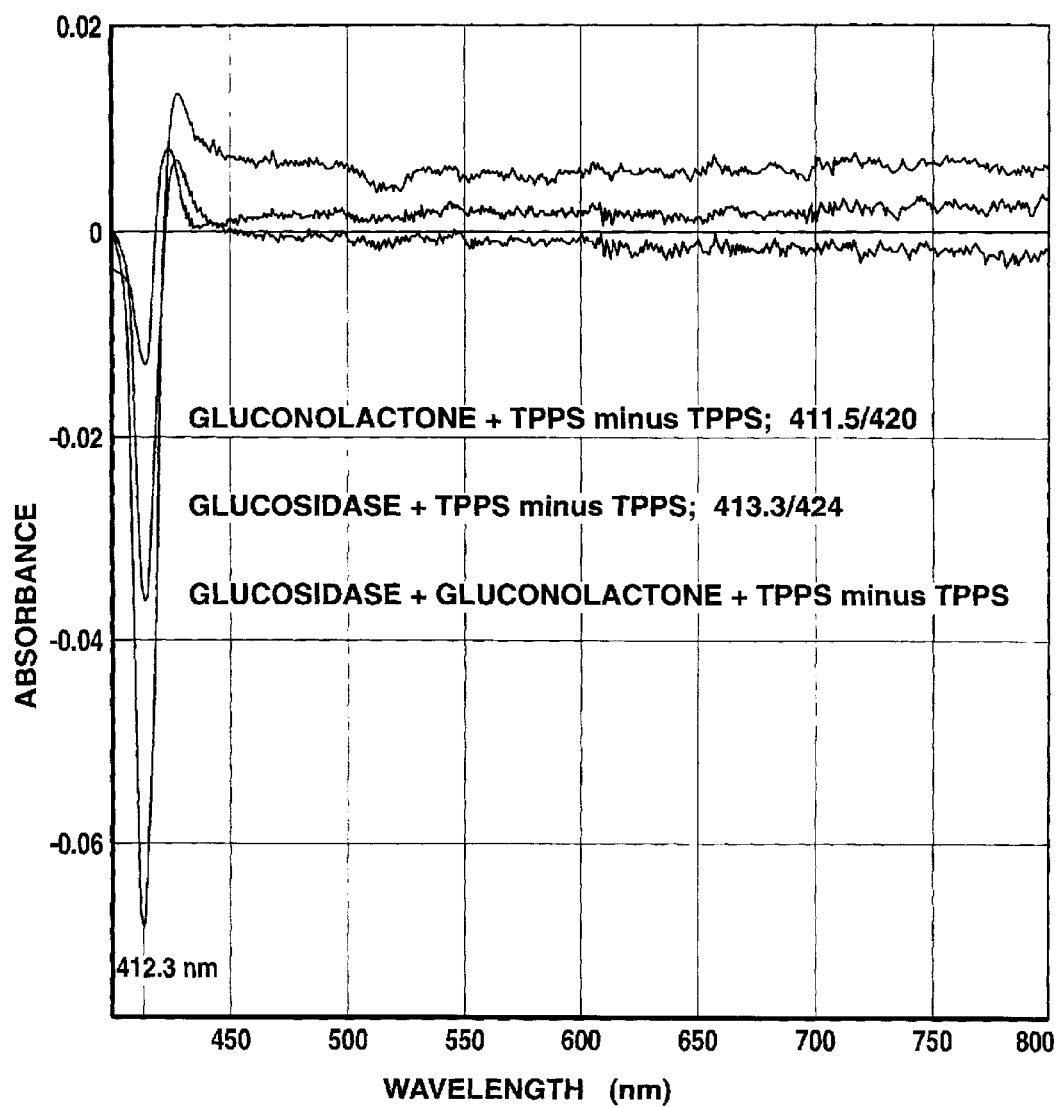
FIG. 4 illustrates the spectra that result in the presence of TPPS for Gluconolactone, Glucosidase, and Glucosidase plus Gluconolactone. The numbers indicate the wavelengths at which absorbance is lost/wavelengths at which absorbance is gained.

Another example of inhibitor-induced conformational change detected by TPPS is seen in the enzyme glucosidase (which breaks down sugars similar to lactose) and its competitive inhibitor gluconolactone. In the absence of gluconolactone, the wavelength of TPPS is shifted to 423 nm by glucosidase (FIG. 4); in the presence of gluconolactone and glucosidase, the wavelength maximum is seen at 425 nm and a loss in 515 nm absorbance (another absorbance band of TPPS) is also seen. In addition, the absorbance changes are significantly larger in the inhibited enzyme.

Based on the forgoing, the instant inventor contemplates that the presence of organophosphates and other nerve agents (inhibitors of AChE) including VX, GA, GB, etc., can be detected as a class of nerve agents from the conformational changes induced by the binding of the inhibitor to AChE, organophosphate hydrolase (binds OP and catalyzes its hydrolytic breakdown), or other enzymes/proteins. Nerve agents such as VX are expected to bind at the active site, and like paraoxon, induce a conformational change in AChE or OP hydrolase. These conformational changes can be detected by several techniques, as indicated earlier, as well as via the following:

1) the intrinsic fluorescence of tryptophan residues in the enzyme might change if/when the hydrophobic/hydrophilic environment of the tryptophan changes as the conformation of the protein changes; and
2) changes in the absorbance and fluorescence of molecules such as porphyrins whose absorbance as well as fluorescence spectra changes as the conformation of the enzyme changes.

In general, the spectrum of porphyrins is unaffected by inorganic molecules like salts unless they induce "stacking" or aggregation (both of which alter the absorbance characteristics and reactive properties of the porphyrin). Preferably, a porphyrin that partitions itself into a region of a protein whose hydrophilic or hydrophobic nature changes as the substrate or inhibitor (better) binds is used as an indicator of conformational change. This may require the use of a porphyrin with different characteristics than TPPS.

Similar detection can be used to detect the presence of inhibitors/substrates/etc of other enzymes and proteins as well.

Thus, a key aspect of the instant invention is the detection of the presence of cholinesterase inhibitors, nerve agents, organophosphates, etc by their binding to the protein acetylcholine esterase or other related ("serine esterase/hydrolase/protease" with a serine in the active site) enzymes, altering the conformational change of the protein. Instead of measuring the loss of enzymatic activity of acetylcholine esterase or serum cholinesterase as is usually done, change in conformation of the enzyme by any inhibitor (hence, broad spectrum) is measured. The measurement involves the use of a "reporter" molecule such as a porphyrin whose absorbance and/or fluorescence spectrum changes as its immediate environment changes. This is a non-specific detector of any cholinesterase inhibitor that alters the conformation of the enzyme. The specificity of the detection of only nerve agents relies on the inherent specificity of acetylcholine esterase and OP hydrolases to only bind these agents or substrate in the active site to the exclusion of other molecules.

A preferred field of application of the instant methods is for use with detection of chemical warfare agents. Of course, it is impossible in most instances to determine the response of the instant invention to lethal chemicals of these sorts. However, it is possible to verify the utility of the methods disclosed herein through the use of analogues (simulants) of organophosphate and sulfur-mustard compounds. For example, the absorbance and fluorescence changes of soluble and immobilized porphyrins and other colorimetric indicators can be measured in the presence of simulant compounds such as DIMP, DMMP, MPA, malathion, parathion (to simulate organo-phosphate agents such as Sarin or VX) and imidazole, methionine, thiodiethanol, cysteine, and other sulfur-containing organic molecules (to simulate mustards). Further, the absorbance/fluorescence changes of porphyrins or other colorimetric compounds associated/incorporated with acetylcholine esterase, OP hydrolase, or other model proteins such as "serine esterases" may be used to simulate the conformational changes in the protein induced by binding of nerve agent/inhibitor.

Preferred Embodiments

When the instant invention is used in practice, the spectral measurements might come from either absorbance, fluorescence, or reflectance spectra. Where absorbance spectra are used, the preferred range of light within which measurements will be taken is the 200–900 nm (UV-VIS) range (suitable at least for chemical warfare agents). Further, it is preferable that either a dual wavelength or dual beam instrument (and procedures) be used. In the preferred embodiment, dual beam spectroscopy is performed using a Cary 4E UV-VIS instrument.

When dual wavelength spectroscopy is to be used, a conventional dual wavelength spectrophotometer would be a suitable instrument. Dual wavelength spectroscopy is ideally suited to measuring absorbance spectra of highly scattering turbid samples and for spectroscopic measurement via fiber optics. Since light is scattered by turbid samples, the detector tends to see the "scatter" as "absorbance" (decrease in light intensity). Further, since shorter wavelengths of light are scattered more than are longer wavelengths, the spectrum of a turbid sample in a dual beam instrument using water or air as reference has a non-flat baseline, making data interpretation difficult if not impossible.

In dual wavelength spectroscopy, two wavelengths of light alternately illuminate the sample, one wavelength being designated as a reference wavelength. Thus, a reference material need not be used. Of course, a reference wavelength should be chosen so as to not coincide with an absorbance peak of the sample. The absorbance of the reference wavelength is the "reference" signal of the system and includes light losses due to the material of the samples as well as the optical system (including cuvettes, holders, optical fibers, etc). Dual wavelength spectroscopy is the technology of choice when it is necessary to measure reflectance spectra, evanescent wave spectra, fiber optically-coupled samples, or solid/suspension/films/slurries, etc. (i.e., high scatter or variable samples, e.g., stirred).

Fluorescence spectroscopy is also suitable for use with the instant invention. Of course, it is based on different principles than absorbance spectroscopy. As is well known to those of ordinary skill in the art, in fluorescence spectroscopy a photon of light is absorbed and then emitted, the emitted photon having a longer wavelength than the photon absorbed. The time interval between absorbance and emission differentiates fluorescence from phosphorescence. The emitted photon is of lower energy (longer wavelength), the wavelength of emitted light being dictated by the energy levels of the electrons of the material.

Spectral Deconvolution of Multiple Peaks

The presence of more than one analyte (a mixture) can be detected via the instant methods since it is quite unlikely that the analytes will have the same spectral signature. For example, if the sample is a mixture of naphthalene and benzene, a loss would be seen at 413 and a gain at 426 nm due to naphthalene and a loss at 413 and a gain at 419 due to benzene. If the monitoring instrument can optically/spectral resolve these 419 and 426 nm peaks, a trough would be seen at 413 nm and peaks at 419 and 426 nm. If the peaks cannot be resolved, a peak and a "shoulder" may be seen (which analyte is the peak and which is the shoulder depends on their relative concentrations). However, both the $\lambda_{max}$ and absorbance of each peak can be determined accurately by calculating the 2nd derivative of the spectra. The wavelengths of the peaks will show up as troughs and the depth of the trough is proportional to absorbance which is proportional to concentration.

Spectra having multiple peaks can be manipulated using software such as Grams/32 (Galactic Industries) for subtractions, smoothing, etc. Spectra, including the 2nd and 4th derivatives or other mathematical manipulations thereof, can be performed using any number of available software products to determine the wavelengths of peaks and troughs and the integrated area under each curve.

Linkage of Detectors to Solid Substrates

Porphyrins and proteins are covalently bound to solid matrices as described earlier. The instant inventor has found three preferred approaches to immobilization that have yielded a reactive porphyrin surface. The first two methods can be used to immobilize proteins.

First, amino-TPPS can be covalently linked to activated Sepharose-CH beads with a 9-atom spacer (Pharmacia) according to manufacturer's directions. One gram of beads is capable of binding 50 mmoles of ligand.

Second, amino-TPPS is bound to polystyrene microtiter plates and microscope slides (Xenobind from Xenopore, Saddle Brook, N.J.) that exhibit spectral changes on metal binding and pH changes.

Finally, TPPS can be covalently linked to dialysis tubing by drying TPPS onto the tubing. The films are washed with 1 M NaCl. The TPPS that is left bound is not removed by acid/base or salt treatment. The absorbance of the bound TPPS is small, but perfectly suited for detection of low levels of analyte using difference spectra as described previously.

Preferred Apparatus

Figure 5:
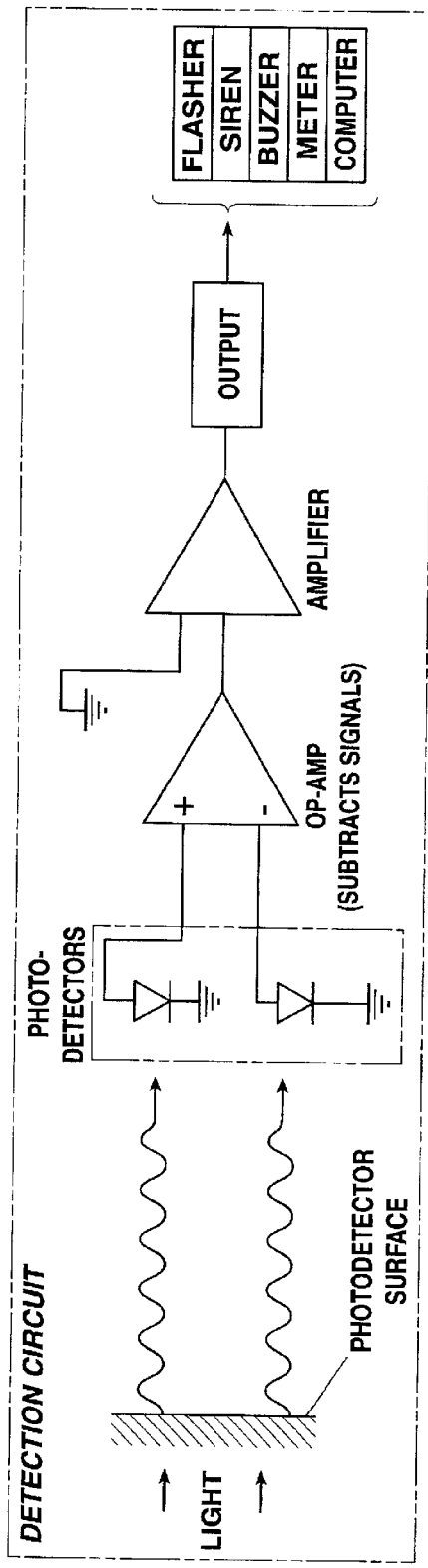
FIG. 5 contains a simplified schematic of an OP detector that implements the method of the instant invention.
Figure 6:
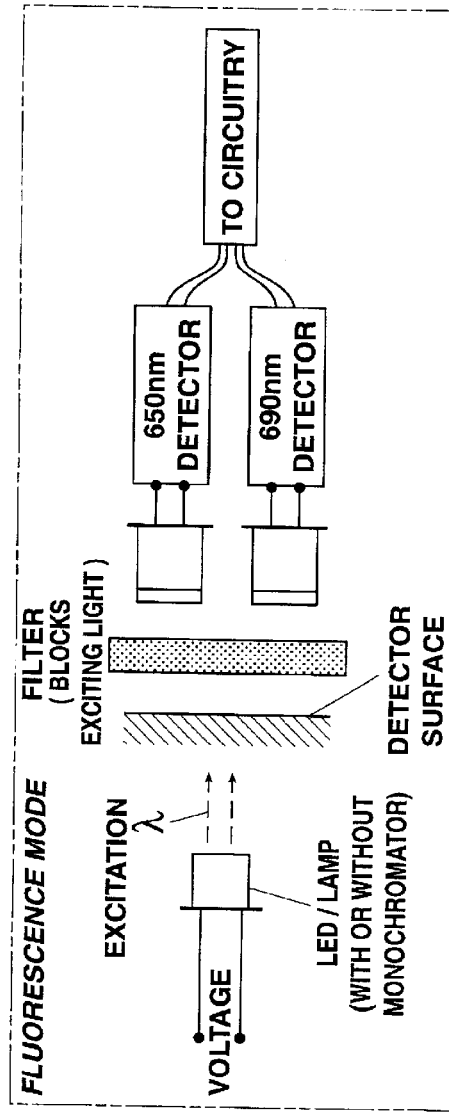
FIG. 6 illustrates an OP detection circuit, wherein a fluorescent light source is used.
Figure 7A:
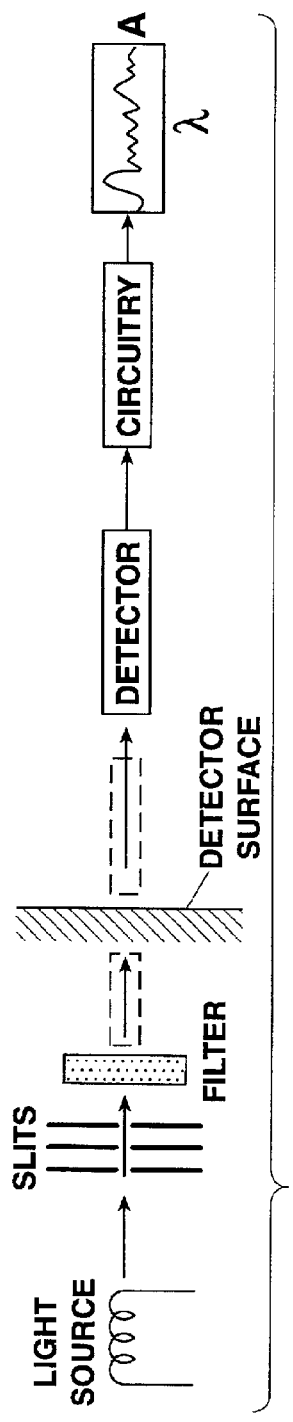
FIGS. 7A–7D contain another OP detector schematic.
Figure 7B:
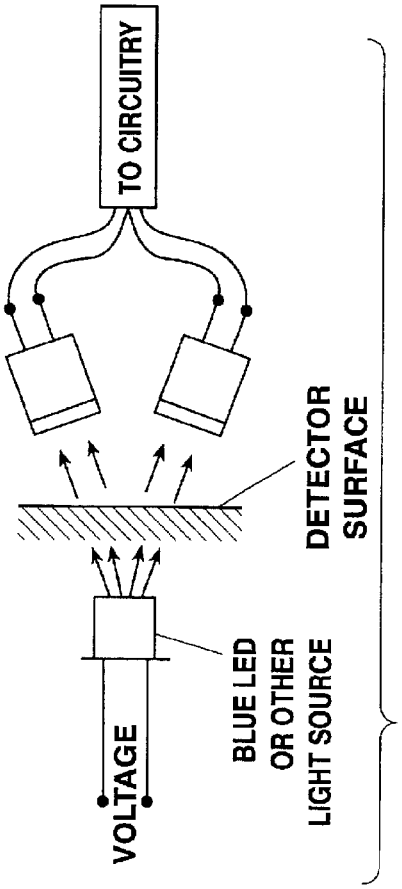
Figure 7C:
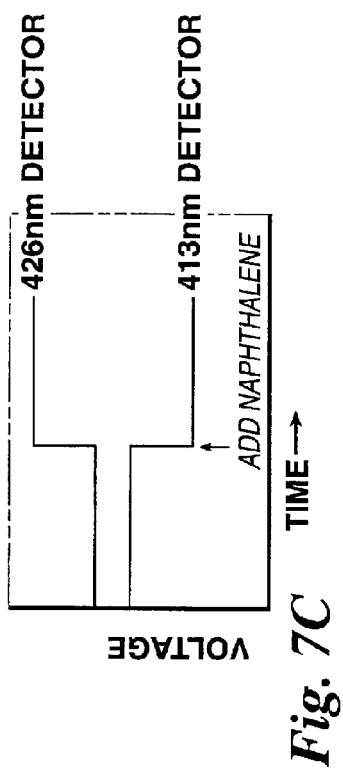
Figure 7D:
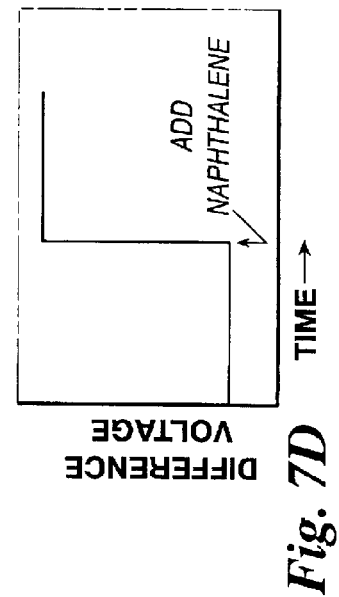

Although the instant invention might be embodied in many forms: FIGS. 5, 6, and 7 contain some presently preferred arrangements. The optical detector of the instant invention consists of several elements. First, there is a light source that can generate a single wavelength of light (e.g., a laser) or more than one wavelength of light (e.g., an LED or lamp with/without filters) that illuminates a detector surface of the type described previously. The light may be shown directly onto the surface or transmitted there via some media such as optical fibers (e.g., FIG. 7). Further, the wavelength of the incident light can be varied through different wavelengths and/or "scanned" across the material so that different wavelengths of light are sequentially striking the material.

The detector material absorbs different amounts of the wavelengths of light falling on it, which produces an absorbance spectrum. The light not absorbed by the material is transmitted to a detector for measurement. Again, the light reflected by the detector material can be directly sensed by a detector or transmitted to a remote detector.

The change in light absorbance by the detector surface material can be measured via a conventional spectrophotometer, where the incident light is scanned through many wavelengths and the amount of light is measured at each of these frequencies to yield a spectrum, similar to that shown in FIGS. 1 to 4. The scanning spectrophotometers can be large bench-based units, "cards" that fit into PC's and connect to the detector surface material via fiber optics, or via laptop and even smaller computers (such as those made by Ocean Optics).

Alternatively, the absorbance at one or two (or, preferably only a few) wavelengths of light can be used to detect the presence of one or a few analytes. For example, the presence of napthalene causes the porphyrin TPPS to lose its absorbance at 413 nm and to gain absorbance instead at 426 nm. In the presence of benzene, the absorbance increases at 419 nm; different analytes absorb at different wavelengths. To determine the amount of napthalene present, only the absorbance decrease at 413 nm and increase at 426 nm need be measured.

FIG. 5 diagrams one possible arrangement of a preferred detector. The light source should be capable of at least emitting light in the general wavelength range shown in Table 2. In the preferred embodiment, the light source will be an LED or other broad band light source, but it is certainly possible that the monochromatic lights sources such as lasers could be used instead. What is important, of course, is that the light source irradiate the photodetection surface with wave lengths of light that at least interact with the specific bands of interest. Continuing with the illustration of the begun previously, the light source should include both 413 nm and 426 nm light.

As is illustrated in FIG. 5, the light will strike two photodiodes/phototransistors/photodetectors that are preferably fitted with narrow filters to admit only light at the specific frequencies of interest, i.e., 413+/−3 nm and 426+/−3–5 nm, respectively, for purposes of the instant example.

The colorimetric detector material surface whose wavelength changes upon reaction with the desired analyte is preferably placed between the LED and the detectors. Alternatively, the LED light can be reflected (bounced off) the material onto the detectors (i.e., a reflectance spectra will be obtained; the same wavelengths of light will be absorbed as in the "head on" configuration.)

The output current or voltage—one can be converted to the other—of the detector is proportional to the intensity of the light striking it. Thus, in the present example, the output of the "413" detector decreases and the output of the "426" detector increase as naphthalene binds to TPPS.

A simple subtraction circuit using, for example, an operational amplifier (or "OP amp", FIG. 5) is a preferred apparatus for analyzing the voltage difference between the two signals; the subtraction of a negative voltage ("413") from a positive voltage ("426") resulting in an effective addition of the two voltage current changes. This arrangement also helps prevents "false" readings. The circuitry can be devised to read or detect only when the output of the one detector goes down and the other goes up. This is a "coincidence" circuit, as both events must occur for the change to be registered. The loss of absorbance because of an increase in light or the gain in absorbance due to clouding or mud (or whatever) is not recorded. For purposes of the instant disclosure, the term "comparator" will be taken to include not only special purpose hardware for comparing signals (such as the differencing units utilized in the preferred embodiment), but also will be taken to encompass hardware/software combinations that allow for more elaborate comparison schemes than differences (e.g., ratios of signals, general linear combinations of signals, products, etc.), whether the operation is performed on an analog or a digital signal.

The output from the optical detectors is conventionally a voltage, with the voltage being proportional to intensity of light in the wavelength monitored which, in turn, is proportional to the amount of analyte that interacts with the detector surface.

In the case of a conformational detection system, the loss of the 413 nm peak of TPPS and an increase at some other wavelength(s) will be recorded as a nerve agent encounters the photodetector surface. Use of a proper filter on the detector allows only the wavelengths of interest to be measured. If a filter is used that passes light from, say, 420 to 430 nm, the wavelengths changes initiated by multiple analyte interactions can be recorded. Unlike the case of measuring napthalene vs. benzene using TPPS where the wavelengths are specific, it is also possible to measure a change of TPPS absorbance (or fluorescence) as the enzyme conformation changes at whatever wavelength; the specificity is not in the particular wavelength measured. The specificity is introduced into the instant system through the fact that the enzyme that will only bind specific inhibitors or substrates.

Figure 8:
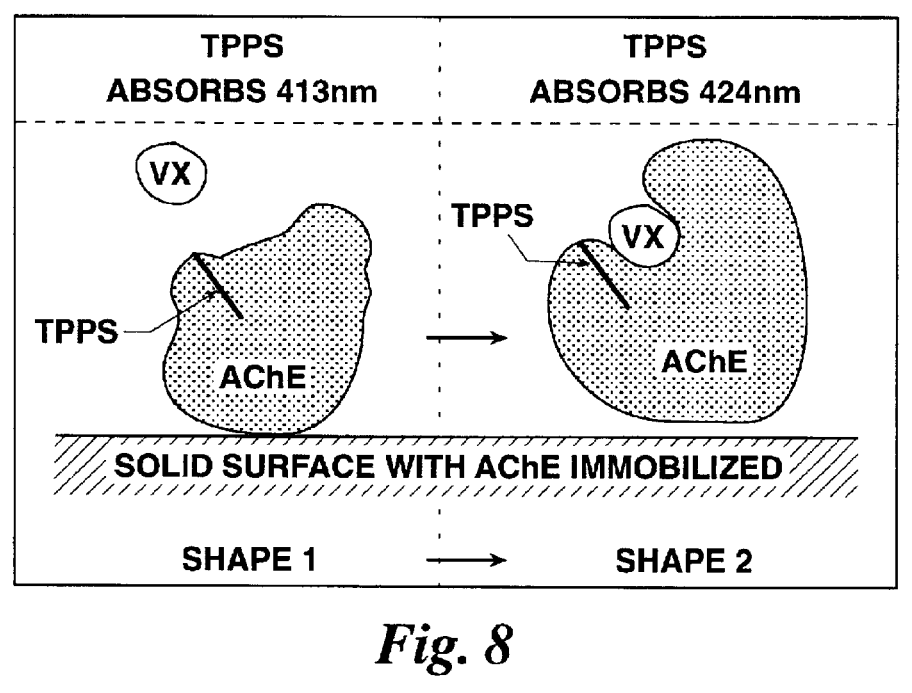

FIG. 6 is a diagram of a fluorescence-based detector where the TPPS absorbs light and emits light at, say, 650 nm. When the protein shape changes (as is schematically illustrated in FIG. 8) and the TPPS is altered, the fluorescence wavelengths are also altered to, say, 690 nm. Thus, the intensity of the 650 nm fluorescence and the fluorescence intensity at 690 nm increases. The circuitry is the same and the additive changes are similar. In the preferred embodiment, the 650 nm and 690 nm detectors are created by placing narrow band optical filters of corresponding wavelengths ahead of broader band photodetectors.

Conclusions

For purposes of the instant invention a colorimetric molecule, indicator, or agent should be interpreted in its broadest sense to include a chemical compound which changes its color, absorbance spectrum, fluorescence spectrum, reflectance spectrum, and/or its fluorescence and polarization properties upon binding of or interaction with another molecule or atom. This term also encompasses those molecules whose spectral properties change upon chemical oxidation or reduction. For purposes of this disclosure, the colorimetric "indicator" can be a colorimetric compound/molecule incorporated into another molecule such as protein, DNA, RNA, nucleic acid, amino acid, peptide, etc.

It should further be noted that, although the previous discussion has principally been concerned with the real-time differencing of spectral intensities using special purpose signal processing hardware, the instant invention would work in exactly the same fashion if the differencing were performed digitally. More specifically, an analog-to-digital conversion of the detected spectral intensity signals can be performed as the information is collected, with the digital output being sent to a microprocessor or a general purpose computer (collectively a "microprocessor", hereinafter) for subsequent digital manipulation. Of course, one advantage of this arrangement is that any mathematical operation—not just differencing—could be used to combine the information from the most recently collected spectral values with those collected earlier.

Additionally, in the preferred embodiment the light source will contain a plurality of light frequencies therein. Of course, those skilled in the art will recognize that, rather than using a single broad-band light source, instead two (or more depending on the application) narrower sources could be used instead.

It should be further noted that measurement of the loss in intensity of the characteristic peak of the AChE-TPPS$_1$ complex (442 nm) upon introduction of a compound can be used to indicate the presence of competitive inhibitors of AChE. As described previously, this is especially useful for detecting the presence of organophosphates, nerve gases, drugs, and pesticides and could possibly be used to detect levels of drugs such as tacrine in the body fluids of patients. More generally, measurement of the spectral change in the TPPS$_1$-AChE complex provides the basis for a detector for any compound which binds at the active site of AChE without requiring a measurement of the catalytic activity of the enzyme before and after exposure. The same concept could be applied to other enzymes which can be shown to bind colorimetric molecules such as porphyrins at or near the active site. Specific inhibitors of this type of enzyme could be detected, provided they cause removal of the colorimetric molecule from the active site.

Finally, the term "real-time" as used herein to describe the instant data collection system should be interpreted to include times up to about one-minute or so. In general, though, the invention is designed to give measure and give feedback on the order of a every few seconds. While the inventive device has been described and illustrated herein by reference to certain preferred embodiments in relation to the drawings attached hereto, various changes and further modifications, apart from those shown or suggested herein, may be made therein by those skilled in the art, without departing from the spirit of the inventive concept, the scope of which is to be determined by the following claims.

What is claimed is:

1. A method of real-time testing for the presence of an analyte in an environment, comprising the steps of:
   (a) obtaining a colorimetric indicator that has been reversibly incorporated into a binding protein, said binding protein having an active site at which the analyte will bind if present, said colorimetric indicator being a porphyrin reversibly bound at said active site to form a complex;
   (b) exposing said complex to said environment;
   (c) measuring at least one spectral value of said colorimetric indicator; and,
   (d) determining from any spectral value so measured whether said colorimetric indicator has been displaced from said binding protein and, thus, whether or not said analyte is present within said environment.

2. A method according to claim 1, wherein step (a) includes the step of immobilizing said complex on a surface.

3. A method according to claim 2, wherein said surface is a microscope slide.

4. A method according to claim 1, wherein said binding protein is AChE.

5. A method according to claim 1, wherein step (c) further includes measuring two spectral values and step (d) further includes determining from said two spectral values so measured whether said colorimetric indicator has been displaced from said binding protein.

6. A method according to claim 5, wherein a first of said two spectral values is measured at about 402 nm and the other at about 442 nm.

7. A method according to claim 1, wherein step (d) includes the steps of:
   (d1) obtaining at least one pre-exposure spectral measurement of said colorimetric indicator and said binding protein before exposure to the sample,
   (d2) calculating at least one numerical difference between said at least one measured spectral values and said at least one pre-exposure spectral measurements.

8. A method of real-time testing for the presence of an analyte in an environment, comprising the steps of:
   (a) obtaining a colorimetric indicator that has been reversibly incorporated into a binding protein, said binding protein comprising AChE having an active site at which the analyte will bind if present, said colorimetric indicator being reversibly bound at said active site to form a complex;
   (b) exposing said complex to said environment;
   (c) measuring at least one spectral value of said colorimetric indicator; and,
   (d) determining from any spectral value so measured whether said colorimetric indicator has been displaced from said binding protein and, thus, whether or not said analyte is present within said environment.

9. A method according to claim 8, wherein step (a) includes the step of immobilizing said complex on a surface.

10. A method according to claim 9, wherein said surface is a microscope slide.

11. A method according to claim 8, wherein two spectral values are measured.

12. A method according to claim 11, wherein a first of said two spectral values is measured at about 402 nm and the other at about 442 nm.

13. A method according to claim 8, wherein step (4) includes the steps
   (d1) obtaining at cast one pre-exposure spectral measurement of said colorimetric indicator and said binding protein before exposure to the sample,
   (d2) calculating at least one numerical difference between said at least one measured spectral values and said at least one pre-exposure spectral measurements.

14. A method of real-time testing for the presence of an analyte in an environment, comprising the steps of:
   (a) obtaining a colorimetric indicator that has been reversibly incorporated into a binding protein, said binding protein having an active sit at which the analyte will bind if present, said colorimetric indicator being reversibly bound at said active site to form a complex;
   (b) exposing said complex to said environment,
   (c) measuring at least two spectral values of said colorimetric indicator, wherein a first of said two spectral values is measured at about 402 nm and the other at about 442 nm; and,
   (d) determining from said spectral values so measured whether said colorimetric indicator has been displaced from said binding protein and, thus, whether or not said analyte is present within said environment.

* * * * *